United States Patent [19]
Josef et al.

[11] Patent Number: 5,869,347
[45] Date of Patent: Feb. 9, 1999

[54] PARTICLE IMMUNOASSAY USING A COMPACT MATRIX

[75] Inventors: Dieter Josef, Cressier; Suzanne Greber, Herrenschwanden; Jean Adam, Villars, all of Switzerland

[73] Assignee: Stiftung fur Diagnostische Forschung Praz-Rond, Morat, Switzerland

[21] Appl. No.: 822,158

[22] Filed: Mar. 17, 1997

[30] Foreign Application Priority Data

Mar. 18, 1996 [EP] European Pat. Off. .............. 96104283

[51] Int. Cl.$^6$ ........................ G01N 33/53; G01N 33/536
[52] U.S. Cl. .......................... 436/536; 436/538; 436/533; 436/534; 422/58; 422/59; 422/60; 422/72
[58] Field of Search ..................... 436/536, 538, 436/541, 533, 534; 422/58, 59, 60, 72

[56] References Cited

U.S. PATENT DOCUMENTS 5,073,344  12/1991  Smith et al. ............................. 422/69

FOREIGN PATENT DOCUMENTS

| | | |
|---|---|---|
| 0 143 412 | 11/1984 | European Pat. Off. . |
| 0 194 212 | 2/1986 | European Pat. Off. . |
| 0 305 337 | 8/1988 | European Pat. Off. . |
| 0 485 228 | 11/1991 | European Pat. Off. . |
| 2 445 528 | 12/1979 | France . |
| 9205440 | 4/1992 | WIPO . |

*Primary Examiner*—Toni R. Scheiner
*Attorney, Agent, or Firm*—Nikaido Marmelstein Murray & Oram LLP

[57] ABSTRACT

This invention relates to a method of detecting an analyte in a test liquid by means of agglutination, with the test liquid being brought into contact with an agglutinin and a reaction between the analyte and the agglutinin determined. In addition, reaction vessels and reagents for implementing the method of the invention are disclosed.

20 Claims, 5 Drawing Sheets

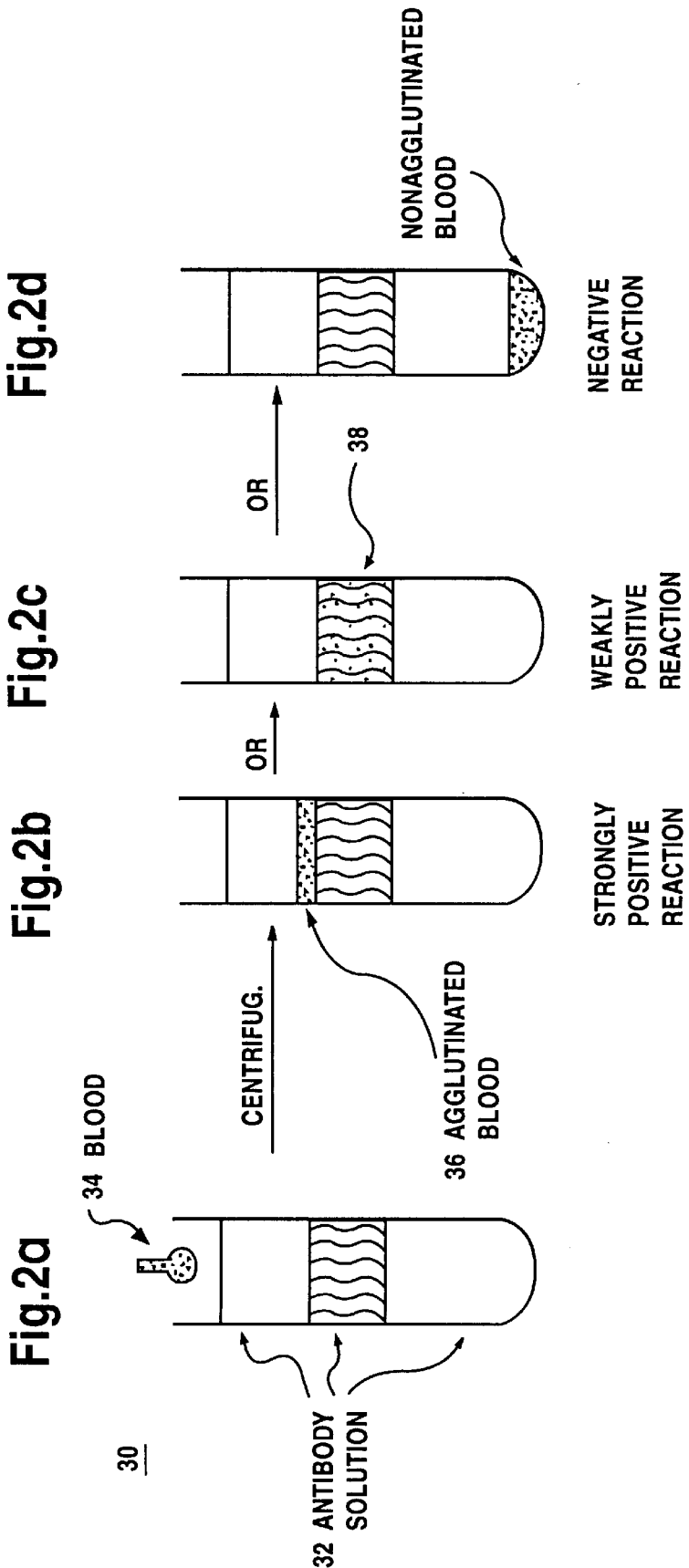

POSITIVE REACTION    NEGATIVE REACTION

PARTICLE IMMUNOASSAY USING A COMPACT MATRIX

SPECIFICATION

This invention relates to a method of detecting an analyte in a test liquid by means of agglutination, with the test liquid being brought into contact with an agglutinin and a reaction between the analyte and the agglutinin determined. In addition, reaction vessels and reagents for implementing the method of the invention are disclosed.

Methods of detecting analytes by means of agglutination are known. For example, in the EP-B-0 194 202 a method of detecting erythrocyte agglutinations is disclosed in which a mixture of serum and erythrocytes is added after incubation to a gel medium which can contain antibodies, whereafter this mixture is subjected to sedimentation conditions which allow the determination of an erythrocyte agglutination.

The EP-A-0 305 337 discloses a method of detecting antibodies or antigens by rendering complexes of carrier-bound antigens with antibodies in aqueous medium visible. According to this method a solution containing an antibody or an antigen is brought into contact with a carrier-bound antigen or antibody respectively, with a slurry or suspension of inert particles being added before, during or after this reaction and the mixture subsequently being exposed to gravitation. In cases where an antigen-antibody complex is formed, this complex will lie on top of the inert-particle sediment if the reaction is strongly positive, and within the inert particles if the reaction is weakly positive. In the absence of an antigen-antibody complex, i.e. if the reaction is negative, the carrier-bound antibodies or antigens will lie underneath the sedimented inert particles. As inert particles use can be made, for example, of dextrose polymers or ballotini.

The use of a gel medium or particle-type matrix can, however, be associated with a number of disadvantages. For one thing, the layer of inert particles is mechanically unstable: the surface can shift when the matrix is disposed horizontally, and vibrations can cause splashing. This means that questionable or even incorrect results are sometimes obtained. In addition, the inert particles have to be made with a very high degree of precision, as otherwise the accuracy and sensitivity of the method can vary too strongly. Besides these disadvantages, it is technically very difficult to dispense suspensions of inert particles in the microliter range, especially since the constant stirring which is required during addition of the inert particles damages them, and this in turn can falsify the volume. Yet another disadvantage of the known method is that it is for the main part limited to colored carrier-bound antigens or antibodies, such as erythrocytes. White or colorless reagents as in the case, for example, of leucocyte, thrombocyte or latex reactions, cannot be detected without prior staining.

One of the objectives underlying the invention described here was thus to eliminate, at least partially, the above-mentioned disadvantages resulting from the use of a matrix consisting of inert particles.

This objective is established by providing a method of detecting an analyte in a test liquid by means of agglutination, the test liquid being brought into contact with an agglutinin and a reaction between the analyte and the agglutinin being determined, wherein use is made of a reaction vessel which contains a compact, porous matrix and which, following the action of gravitational forces, allows qualitative or semi-quantitative determination of the agglutination reaction.

Surprisingly, it was found that all the seemingly insoluble problems which result from the use of inert particles can be overcome by using a single, compact matrix instead of the individual inert particles.

For the method of the invention use is made preferably of a compact matrix which contains ducts, in particular ducts of a defined diameter. The internal diameter of the pores, or ducts, of the matirx can vary according to the test in question. For example, pores of a smaller diameter are used for small thrombocytes than those used for the relatively large leucocytes.

The compact matrices are available with different pore sizes, as shown in the following table:

| Designation | Designation ISO 4793 | Nominal pore sizes μm |
|---|---|---|
| G0 | P 250 | 160–250 |
| G1 | P 160 | 100–160 |
| G2 | P 100 | 40–100 |
| G3 | P 40 | 16–40 |
| G4 | P 16 | 10–16 |
| G5 | P 1.6 | 1.0–1.6 |

Use is made preferably of a compact matrix based on glass or plastics. Particular preference is given to a glass matrix, e.g. a matrix of Controlled Pore Glass. Such matrices are made, e.g., of Duran. These are available with different pore diameters from the company Brand in Germany. In order to avoid possible non-specific absorptions, the glass is preferably used with a modified surface, e.g. a silanized surface.

The method of the invention relates to the detection of an analyte in a test liquid. As test liquid use is made preferably of body fluids—which may be diluted—such as blood, serum or plasma. The volume of test liquid for the method of the invention can vary over a wide range; for microtests use is made preferably of volumes from 1 to 200 μl.

For detection of the analyte use is made of an agglutinin, i.e. a substance which binds specifically and with high affinity to the analyte. The agglutinin has at least two binding sites for the analyte, which allows the formation of inter-linked agglutination complexes of analyte and agglutinin. In cases where use is made of an immobilized antibody, e.g. an antibody bound to the matrix, a single binding site is naturally sufficient.

The analytes which can be detected using the method of the invention are substances which have a high affinity for and can specifically engage the agglutinin, e.g. antigens and antibodies, which can be determined by means of an immune reaction. A first preferred embodiment of this invention relates to the detection of antibodies as analytes in the test liquid, e.g. antibodies against pathogens such as viruses (HIV, hepatitis viruses), bacteria or protozoa, antibodies against autoantigens, antibodies against tumors or antibodies against allergens. The antibodies can be free antibodies, e.g. IgG, or cell-bound antibodies, e.g. IgE. For the detection of free antibodies, i.e. more specifically, of non-cell-bound antibodies, it is expedient to use a carrier-bound antigen as agglutinin. Examples of suitable carriers are synthetic carriers such as particles of latex, dextrose, agarose, cross-linked polypeptides etc., and natural carriers such as cells, e.g. erythrocytes. Use is made preferably of labelled carriers, i.e. carriers provided with a detectable group. When colored carriers such as erythrocytes are used the additional use of labelling groups is not necessary. It is also possible, with certain embodiments of the invention, to dispense completely with labelling groups. This is explained in more detail below.

Another preferred embodiment of the invention relates to the detection of antigens in a test liquid, e.g. free antigens such as serum proteins, metabolites, hormones, mediators etc., or carrier-bound antigens such as cellular blood-group antigens etc. For the detection of carrier-bound antigens use is made preferably of free antibodies or bivalent fragments thereof as agglutinin. For the detection of free antigens use is made preferably of carrier-bound antibodies or carrier-bound antibody fragments.

According to the method of the invention use is made of a reaction vessel which has a compact, porous matrix and which, following the action of gravitational forces, allows qualitative or semi-quantitative determination of the agglutination reaction between the analyte being assayed and the agglutinin. Although sedimentation can be effected slowly by virtue of gravity, it is of advantage to use a centrifuge, since the desired sedimentation can then be effected in a short time. The optimum conditions with respect to centrifugation time and the g-number can be determined without difficulty by persons versed in the art for any type of assay. These conditions are governed in particular by the consistency of the agglutination complex between agglutinin and analyte, the components of the reaction mixture in the non-bound state and the compact matrix pore size or pore size distribution.

The pore size for the matrix is preferably selected such that in the case of a strong agglutination the reaction product of the analyte being assayed and the agglutinin cannot penetrate to any substantial degree into the compact matrix. This reaction pattern is is explained for example in FIG. 2b and FIG. 3c.

In the case of a weakly positive reaction between the analyte and the agglutinin it is preferable if the the reaction product penetrates into but does not pass through the compact matrix completely. This reaction pattern is explained in FIG. 2c. In the absence of a significant agglutination reaction between the agglutinin and analyte being assayed, components contained in the reaction vessel—especially carrier-bound antobodies, antigens or a carrier-bound agglutinin—can pass through the compact matrix more or less completely. A reaction pattern of this sort is shown in FIG. 2d and FIG. 3d. When use is made of a reaction vessel in which the matrix does not reach to the bottom, it is possible in the case of negative reactions also to determine non-stained carriers, since the sediment is separated from the matrix by a layer of liquid. In the case of weakly positive reactions, the height of the sediment allows a semi-quantitative measurement.

In certain embodiments of the method according to the invention the agglutinin and the analyte can be mixed while both components are in contact with the matrix. In other embodiments, however, preliminary incubation is necessary. This preliminary incubation can take place in a separate vessel. It is preferable, however, if it takes place in the same reaction vessel that contains the matrix. In the latter case the reaction vessel must be designed such that there is no immediate contact between solutions pipetted into the vessel and the matrix. This can be achieved, for example, by providing a membrane above the matrix or—as is explained in detail below by using specially shaped reaction vessels.

The invention will now be explained in detail by reference to the drawings.

FIG. 2 shows the reaction—in a reaction vessel of the type shown in FIG. 1a—of a carrier-bound antigen in a test liquid with an agglutinin;

Figure 1A:
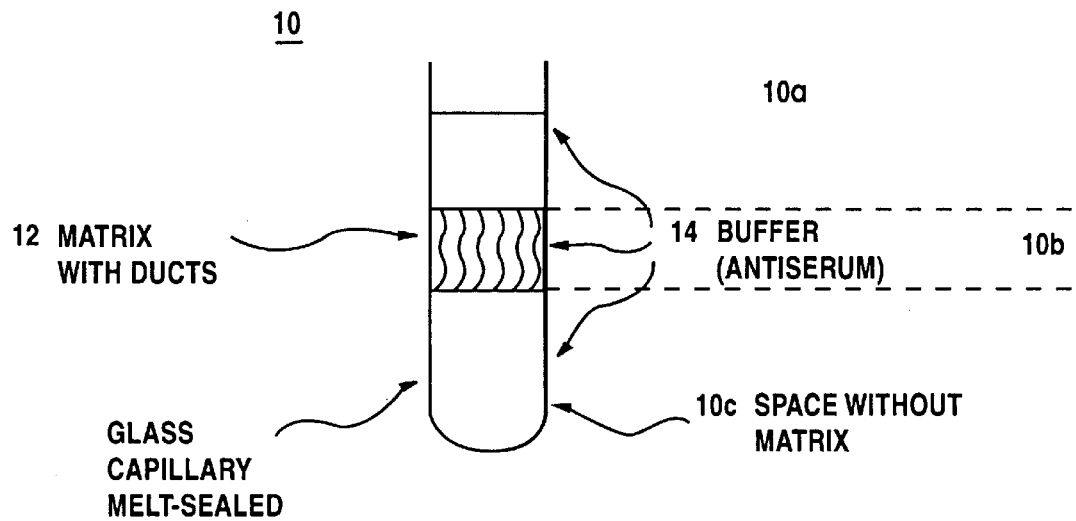
FIG. 1a shows a first embodiment of a reaction vessel in sectional view, with a compact matrix and ducts, for example a commercially available glass capillary which contains an integrated matrix.
Figure 1B:
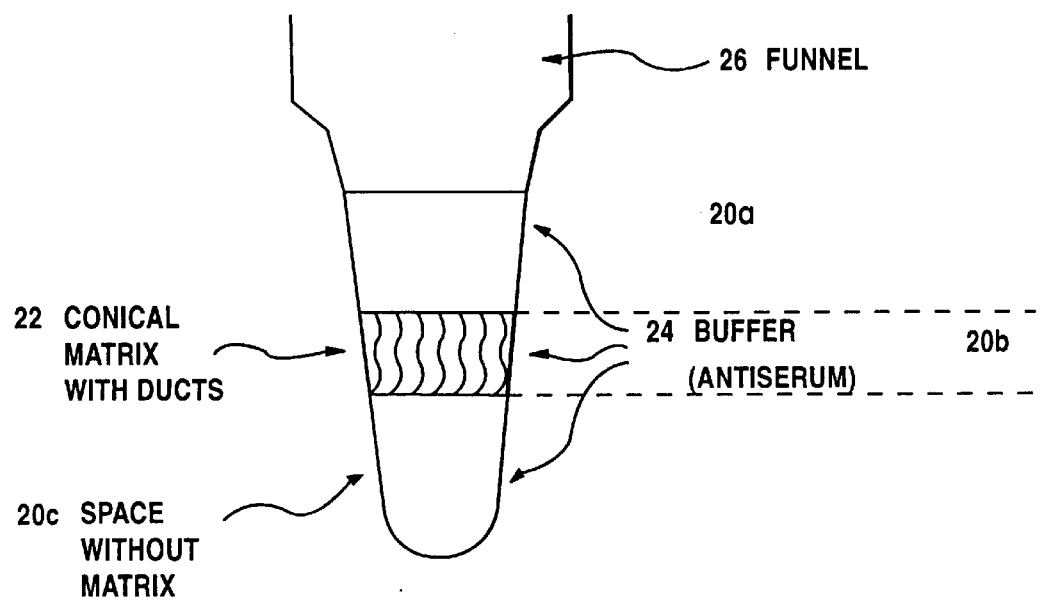
FIG. 1b shows a second embodiment of a reaction vessel in sectional view, with a compact matrix and ducts, for example microreaction vessels such as are available commercially, e.g. from DiaMed and Ortho, and which contain an integrated matrix.

FIGS. 1a and 1b show two preferred embodiments of reaction vessels according to the invention. These reaction vessels (10, 20) have an upper area (10a, 20a), a middle area (10b, 20b) and a lower area (10c, 20c), with a compact porous matrix (12, 22) extending over the middle area (10b, 20b) and the upper (10a, 20a) and lower (10c, 20c) areas comprising a space without a matrix. The reaction vessel also contains a liquid (14, 24), e.g. a buffer or reagent solution, the liquid level of which is higher than the upper end of the matrix. The reaction vessel (20) shown in FIG. 1b has in addition, in the upper area (20a), an extension (26), e.g. in the form of a funnel.

As reaction vessels use is made preferably of microcentrifugation tubes with a volume of 50 $\mu$l to 2 ml, more specifically 50 $\mu$l to 1 ml. When use is made of a microcentrifugation tube (20) with an extension (26), it is of advantage if, prior to addition of the agglutinin to the sample, the liquid level is below the extension (26), so that when the sample and the agglutinin are pipetted an air bubble is able to form which prevents the liquids being added by pipette from making immediate contact with the matrix.

Depending on its design, the reaction tube can be fitted with the matrix and filled with reagent (buffer or antiserum) in different ways. The following procedure is recommended: From a commercially available glass frit a piece which fits the opening is removed and inserted into the capillary. The latter can be joined with the matrix simply by heating. The capillary is now dipped into the reagent, whereupon it fills by simple capillary action. As a result liquid is drawn in and the air is pressed out from the bottom. Depending on the liquid level desired, the procedure can be interrupted at any time. The reaction tube shown in FIG. 1a is obtained by simple sealing-off. If the tube is to be stored for any length of time it may be necessary to seal off the upper end as well. When the tube is needed, the upper end is simply broken off, possibly with the help of a break-off groove. The manual production method described here can of course be mechanized very cost-effectively with the technical means available these days, and the tubes produced in large numbers.

The following procedure is recommended for filling reaction vessels of the type shown in FIG. 1b: the required agent is filled into the slightly conical vessel and then the matrix, which is likewise slightly conical, is added. The matrix comes to fit exactly against the vessel wall by virtue of gravity. This process can of course be accelerated by centrifugation and the fit rendered firmer. A third production method is recommended for reaction vessels of the type shown in FIG. 4, which are designed for horizontal application: the matrix is fitted into the tube prior to the addition of reagent. The reagent is filled into the bulge of the tube and transferred to the lower part by centrifugation, the matrix thereby being pressed simultaneously against the wall of the tube while the air in the tube is pressed out. Industrial-scale production according to this method is also easy to realize.

Antigens or antibodies can be immobilized at the surface of the matrix for certain embodiments of the method according to the invention.

FIG. 2 shows a reaction scheme for the detection of a carrier-bound antigen in a test liquid, e.g. the determination of a blood group characteristic in a patient's sample, using the reaction vessel shown in FIG. 1a and antibodies as agglutinin.

To this end a test liquid (34), e.g. blood, which contains a carrier-bound analyte, e.g a blood group characteristic bound at the surface of erythrocytes, is introduced into a reaction vessel (30) having a compact matrix and in which there is a solution (32) containing antibodies against the analyte being assayed (FIG. 2a). Following centrifugation one finds, in the case of a strongly positive agglutination reaction (FIG. 2b), a band of agglutination products (36) on the upper side of the matrix. If the reaction is only slightly positive, the agglutination product (38) is found within the compact matrix (cf. FIG. 2c). If the reaction is negative, i.e. if the sample contains no analyte and no reaction can take place with the agglutinin, the nonagglutinated carrier-bound components of the reaction mixture (40) settle by virtue of gravity at the bottom of the reation vessel (cf. FIG. 2d).

Figures 3A, 3B:
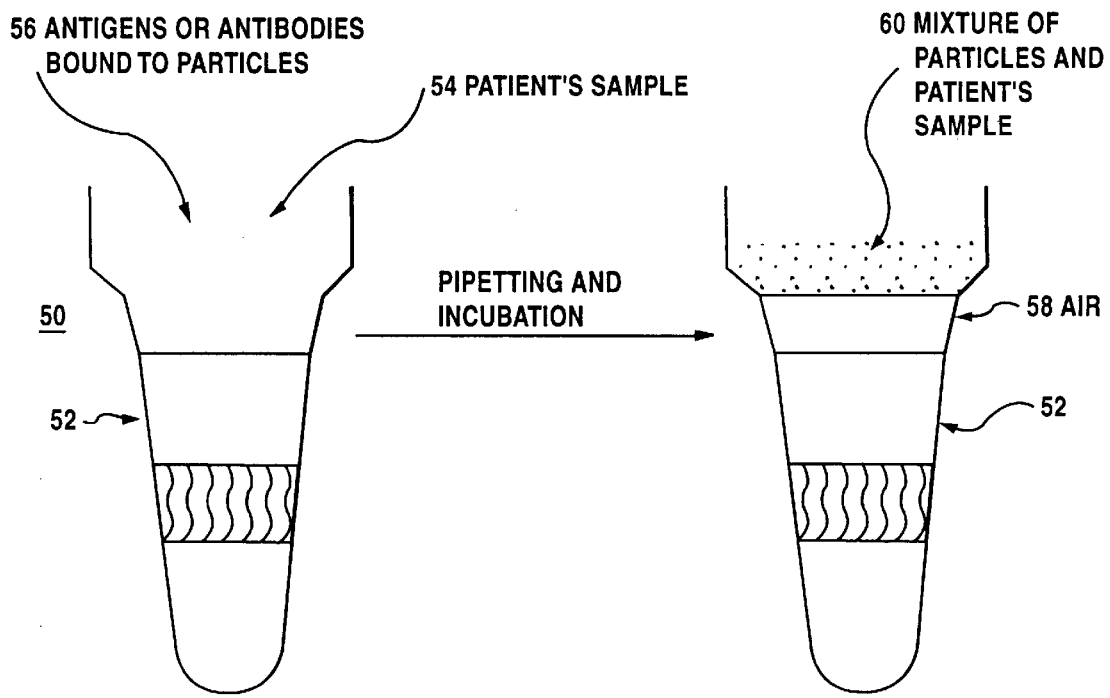
FIG. 3 shows the reaction—in a reaction vessel of the type shown in FIG. 1b—of a carrier-bound agglutinin with a specific antibody in a test liquid.
Figures 3C, 3D:
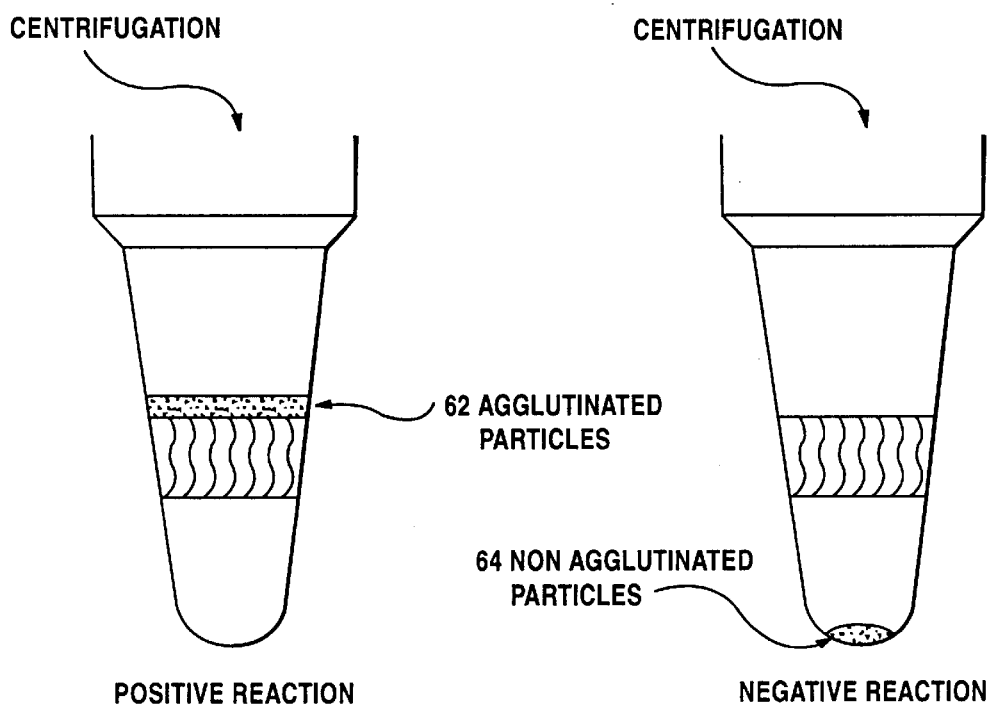

FIG. 3 shows a reaction scheme for the detection of specific antibodies present in the test liquid, using a carrier-bound antigen as agglutinin in a reaction vessel according to FIG. 1b. To this end a test liquid (54) and a carrier-bound antigen, e.g. an antigen (56) attached to the surface of latex particles, are introduced into a reaction vessel (50) which contains a suitable liquid (52), e.g. a buffer solution or a second antibody (Coomb's test). It is of advantage if the addition ensues in such manner that the test liquid and the carrier-bound antigen result in a mixture (60) which is separated from the liquid (52) by an air bubble (58) (cf. FIG. 3b). After a suitable incubation period the mixture (60) is brought into contact with the matrix, e.g. by means of centrifugation. If the reaction is positive, an agglutination product (62) forms on the upper side of the matrix (cf. FIG. 3c), whereas if the reaction is negative, the non-agglutinated agglutinin, i.e. the carrier-bound antigen (64) passes through the ducts of the matrix and forms a sediment at the bottom of the reaction vessel (cf. FIG. 3d).

It is of advantage when implementing the method of the invention to use microreaction vessels which can be disposed adjacent to one another in any desired number on a card or disk. A test card of this kind can be made in various ways. For example, the tubes can be stuck onto a card or disk, or else the tubes and the card or disk can be of integral design.

The reaction vessels can already contain an agglutinin, being sealed with welded-on film. A test prepared in this way makes for easy handling and can be used in an automated assay procedure. The addition of sample to the individual tubes, the sample treatment and the evaluation can be controlled by means of electronic data processing.

The compact matrix moreover makes a surprising method possible with which agglutination reactions can be automated particularly easily and cost-effectively. To this end use is made of reaction vessels (70) of the type shown in FIG. 4. Reaction vessels of this kind have a matrix with ducts (72) as well as a space without a matrix (74), and are filled to a level above the upper end of the matrix with a suitable liquid (76), e.g. buffer or antiserum. In addition, the reaction vessels exhibit an extension (78), e.g. in the form of a bulge, The reaction vessels are preferably attached or integrated horizontally—in any desired number—on a disk (FIG. 5). The resulting simplicity—hitherto not achieved—of the reaction steps is explained in the flow chart shown in FIG. 6: in the first step, the reagent required for the particular reaction, be it buffer or antiserum, is pipetted into the bulge of the tube. By means of centrifugation the liquid is transferred to the lower part of the tube, the air in the tube being pressed out at the same time. This first step can ensue either directly before the actual assay, or earlier in an industrial production process. In the latter case the reaction vessels must obviously be tightly sealed, for example by welding on a covering film. In the 2nd step the patient's sample and, in reactions according to FIG. 3, particle-bound antigen, is introduced into the bulge. In the 3rd step antigens and antibodies react in the incubation phase. With reactions according to FIG. 2, this step can of course be omitted. The 4th step is centrifugation, resulting in reaction patterns as shown in FIGS. 2b, 2c, 2d. These reaction patterns are read automatically (e.g. by means of a scanner) in the 5th step and interpreted in a computer program. The 6th step is that of data collection; for added certainty, each result can be verified visually.

A further subject of this invention is a reagents kit for detecting an analyte in a test liquid by means of agglutination, comprising
(a) a reaction vessel which contains a compact, porous matrix and
(b) an agglutinin capable of forming agglutination complexes with the analyte.

The reaction vessel and the agglutinin can be physically separate from each other. With certain test formats, on the other hand, the agglutinin can already be in the reaction vessel. It is of advantage to fit the compact matrix into the reaction vessel in such manner that no displacement occurs on centrifugation. It is furthermore expedient to have the matrix in direct contact with the inside of the reaction vessel, so that on centrifugation no components of the reaction mixture can pass between the inside wall of the reaction vessel and the matrix. It is of advantage not to have the matrix extending over the entire area of the reaction vessel but only over a middle area.

In a preferred embodiment of this invention the reagents kit contains a plurality of reaction vessels which are disposed jointly on a card or disk. The reaction vessels on a card or disk can serve for the detection of the same or of different analytes. The volume of the reaction vessels is preferably in the range from 50 $\mu$l to 2 ml.

Yet another subject of this invention is a reaction vessel which contains a compact, porous matrix, the matrix being disposed such that on centrifugation of the vessel there is no displacement of the matrix within the vessel. It is of advantage if the reaction vessel is at least in part optically transparent, so that it is easy to determine whether an agglutination reaction has taken place or not.

The invention is explained in more detail by means of the following examples.

EXAMPLE 1

Production of the Reaction Vessels a) The compact matrix is cut out of frit material (Duran, the company Brand, Germany) such that it has the required shape (FIG. 1a or 1b).

b) The compact matrix is boiled in aqua regia (1 part HNO$_3$ and 3 parts HCl) for 5 minutes to activate it, washed thoroughly in distilled water, dried and then silanized at room temperature for 30 minutes with tetramethoxy silane, Fluka (0.001% in dry methanol), washed with distilled water and dried.

c) For reactions in glass capillaries (FIG. 1a), the silanized matrix is subsequently introduced into these and joined to the glass wall of the capillary by brief heating. For reaction vessels of the type shown in FIG. 1b, with a conically shaped matrix, this step is unneccessary, since, by virtue of its shape, the matrix is fixed automatically in the desired position in the reaction vessel.

EXAMPLE 2

Figure 4:
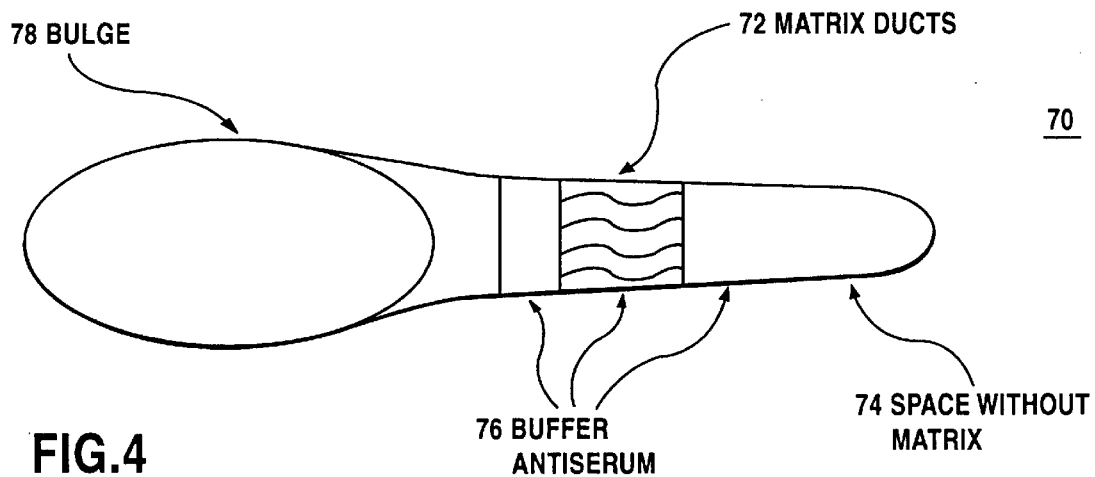
FIG. 4 shows a third embodiment of a reaction vessel in plan view, with the tube for the tests disposed horizontally; through use of a compact matrix the surface of the matrix cannot deform.
Figure 5:
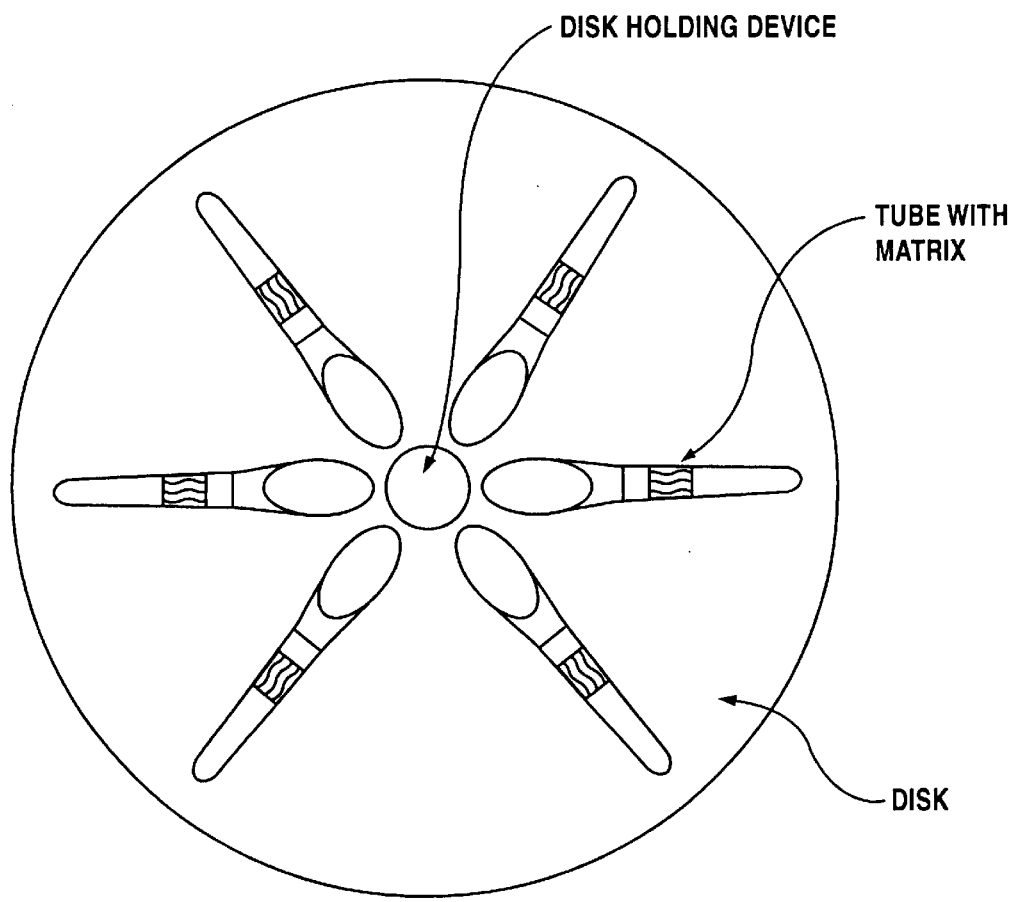
FIG. 5 shows a possible arrangement of reaction vessels according to FIG. 4 on a round disk.
Figure 6:
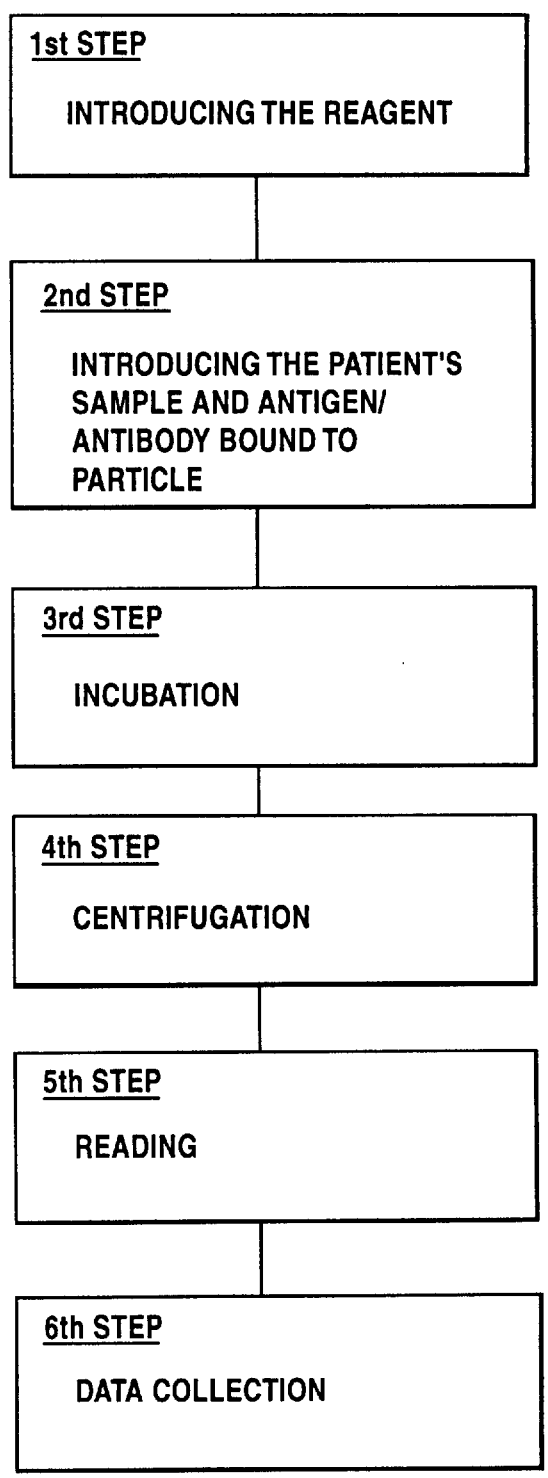
FIG. 6 is a flow chart with which the assaying of analytes using the arrangement shown in FIG. 5 can easily be automated.

Filling the Reaction Vessels a) A glass capillary of the type shown in FIG. 1a is dipped into the desired buffer or antisera solution; as a result of the capillary forces the capillary fills automatically to the desired level, preferably somewhat above the compact matrix. After filling, the bottom of the capillary is sealed by melting or else with lute. The upper end of the capillary can be tightly sealed in this way too. The upper end of the capillary is provided with a break-off goove, e.g. of the type known from ampoules, for use.

b) In the case of reaction vessels of the type shown in FIG. 1b, the buffer or antiserum is filled into the reaction vessels first and the compact matrix fitted subsequently. Once filled, the reaction vessels can be sealed with no problem using known methods.

c) In the case of reaction vessels of the type shown in FIGS. 4 and 5, the buffer or antiserum is introduced into the bulge and transferred to the lower part of the tube by means of centrifuging briefly (5 minutes, 900 rpm).

EXAMPLE 3

Testing for Blood Group A a) Testing in a capillary of the type shown in FIG. 1 a A glass capillary (100 µl) is fitted with a compact matrix (G1) as in Example 1 and dipped, as in Example 2, into a commercially available anti-A reagent (DiaMed). As soon as the liquid level has risen above the matrix, the capillary is withdrawn and is sealed off at the bottom by heating it briefly. Then 50 µl of a 5% suspension (0.9% NaCl) of patient's blood are added and centrifuged in a Heraeus centrifuge at 1000 rpm for 6 minutes. If the reaction is positive, the agglutinated erythrocytes will be on top of the matrix (FIG. 2b) and if the reaction is negative the free erythrocytes will be at the bottom of the capillary (FIG. 2d).

b) Testing in reaction vessels of the type shown in FIG. 1b

The reaction vessels (DiaMed) are made as described in Example 1 and filled, as decribed in Example 2b, with 25 µl of anti-A. Then 20 µl of a 5% suspension (0.9% NaCl) of patient's blood are added and centrifuged for 10 minutes at 910 rpm (centrifuge DiaMed). The eaction patterns are the same as in Example 3a.

c) Testing on a disk as shown in FIG. 5

The reaction vessels (FIG. 4) are made as described in Examples 1 and 2c and filled with 25 µl of anti-A. Then 20 µl of a 5% suspension of patient's blood are introduced into the bulge and the disk centrifuged for 10 minutes at 910 rpm in a centrifuge (DiaMed) adapted for disks. The reaction pattern is the same as in Examples 3a and 3b.

EXAMPLE 4

Detection of Antibodies Directed Against Antigens on Erythrocytes

The reaction vessels are made as described previously and filled with an antibody solution. In this case, however, Coombs serum (anti-human IgG) is used in place of anti-A. Suitably filled vessels which have a funnel (FIG. 2b) or a bulge (FIG. 4) are filled with 50 µl of a 0.8% erythrocyte suspension (test cells DiaMed) and mixed with 25 µl of patient's serum. In the funnel (FIG. 1b) or the bulge (FIG. 4) the mixture of test cells with serum is incubated for 15 minutes at 37° C. Following centrifugation, the reaction patterns are the same as in the previous examples. In the case of a weak antibody reaction, the reaction pattern corresponds to that of FIG. 2c.

We claim:

1. A method of detecting an analyte in a test liquid, comprising providing a reaction vessel which defines a reaction space therein and comprises a unitary matrix which defines ducts therein, wherein the reaction space is located in liquid communication with the unitary matrix;

introducing into the reaction space a test liquid which may contain an analyte to be detected and an agglutinin; and subjecting the test liquid and the agglutinin to a gravitational force, wherein when the analyte is present and a strong positive reaction occurs between the analyte and the agglutinin, the analyte and the agglutinin form an agglutination product which avoids substantial penetration into the ducts, when the analyte is present and a weak positive reaction occurs between the analyte and the agglutinin, the analyte and the agglutinin form an agglutination product which penetrates but substantially avoids passing through the ducts, and when the analyte is absent and a negative reaction occurs between the analyte and the agglutinin, the test liquid comprises non-agglutinated components which pass substantially through the ducts.

2. The method of claim 1, wherein the matrix comprises glass or plastic.

3. The method of claim 2, wherein the matrix comprises glass having a modified surface.

4. The method of claim 2, wherein the matrix comprises silanized glass.

5. The method of claim 1, wherein the analyte is a free antibody and the agglutinin is a carrier-bound antigen.

6. The method of claim 1, wherein the analyte is a carrier-bound antigen and the agglutinin is a free antibody, or fragment thereof.

7. The method of claim 1, wherein the analyte is a free antigen and the agglutinin is a carrier-bound antibody, or fragment thereof.

8. The method of claim 1, wherein the test liquid and the agglutinin are premixed before said introducing step.

9. The method of claim 1, wherein the test liquid and the agglutinin are introduced sequentially in said introducing step.

10. The method of claim 1, wherein the reaction vessel has an upper area defining the reaction space, a middle area containing the matrix, and a lower area defining a space without the matrix, and the non-agglutinated components which pass substantially through the ducts contact the space in the lower area.

11. The method of claim 10, wherein the upper area comprises an extension forming a funnel or a bulge.

12. The method of claim 1, wherein the reaction vessel has a volume of 50 µl to 2 ml.

13. A reagent kit suitable for detecting an analyte in a test liquid, comprising
- a reaction vessel which defines a reaction space therein and comprises a unitary matrix which defines therein ducts having a predetermined uniform diameter, wherein the reaction space is located in liquid communication with the unitary matrix; and
- an agglutinin which is capable of forming an agglutination product with the analyte.

14. The reagent kit of claim 13, wherein the reaction vessel has an upper area defining the reaction space, a middle area containing the matrix, and a lower area defining a space without the matrix.

15. The reagent kit of claim 13, wherein a plurality of reaction vessels are disposed jointly on a card or disk.

16. The reagent kit of claim 13, wherein the reaction vessel has a volume of 50 µl to 2 ml.

17. A reaction vessel which defines a reaction space therein and comprises a unitary matrix which defines therein ducts having a predetermined uniform diameter, wherein the reaction space is located in liquid communication with the unitary matrix, wherein the unitary matrix is disposed in the reaction vessel such that upon centrifugation, displacement of the unitary matrix within the vessel is avoided and no liquid passes between an inside wall of the vessel and the unitary matrix.

18. The reaction vessel of claim 17, wherein the reaction vessel has an upper area defining the reaction space, a middle area containing the matrix, and a lower area defining a space without the matrix.

19. The reaction vessel of claim 18, wherein the upper area comprises an extension forming a funnel or a bulge.

20. The reaction vessel of claim 17, wherein the reaction vessel has a volume of 50 µl to 2 ml.

* * * * *